(12) United States Patent
Krug

(10) Patent No.: US 7,304,306 B1
(45) Date of Patent: Dec. 4, 2007

(54) DIRECT CONVERSION SYSTEM FOR SECURITY STANDOFF DETECTION

(75) Inventor: Florian Krug, Munich (DE)

(73) Assignee: General Electric Company, Niskayuna, NY (US)

(*) Notice: Subject to any disclaimer, the term of this patent is extended or adjusted under 35 U.S.C. 154(b) by 56 days.

(21) Appl. No.: 11/287,725

(22) Filed: Nov. 28, 2005

(51) Int. Cl.
*G01N 21/25* (2006.01)
(52) U.S. Cl. ................................... 250/341.1
(58) Field of Classification Search ............. 250/341.1
See application file for complete search history.

(56) References Cited

U.S. PATENT DOCUMENTS 6,815,683 B2 * 11/2004 Federici et al. .......... 250/341.1
2001/0033636 A1  10/2001 Hartick et al. ................. 378/88
2002/0067480 A1   6/2002 Takahashi .................... 356/317
2002/0074500 A1   6/2002 Mickan et al. ........... 250/341.8

FOREIGN PATENT DOCUMENTS

| GB | 2399626 A | 9/2004 |
| GB | 2411093 A | 8/2005 |
| WO | WO2004/083796 A1 | 9/2004 |
| WO | WO2005/080947 A1 | 9/2005 |

* cited by examiner

*Primary Examiner*—Constantine Hannaher
(74) *Attorney, Agent, or Firm*—Fletcher Yoder

(57) ABSTRACT

A security detection system includes a radiation source configured to generate and direct terahertz radiation onto an object. Further, the system also includes a detector module configured to detect and process radiation from the object, the detector module comprising a parallel arrangement of at least two low noise amplifiers, each operable in a respective frequency band.

26 Claims, 5 Drawing Sheets

DIRECT CONVERSION SYSTEM FOR SECURITY STANDOFF DETECTION

BACKGROUND

The invention relates generally to apparatus and methods for imaging in the Terahertz (THz) frequency range, and more specifically to examining a sample containing an explosive material.

Over the past several years, there has been an emerging interest in the potential of THz detection for security related applications such as imaging of concealed weapons, explosives and chemical and biological weapons. Terahertz radiation is readily transmitted through most non-metallic and non-polar media, which advantageously enables the THz systems to "see through" concealing barriers such as packaging, clothing, shoes, book bags, for example, in order to probe any potentially dangerous materials contained within. Additionally, many materials of interest for security applications including explosives and chemical and biological agents have characteristic THz spectra that may be used to fingerprint and thereby identify these concealed materials. Thus, the combination of transparency to clothing and packaging combined with spectroscopy of illicit materials such as narcotics, biological weapons or explosives may facilitate detection and identification of many different types of materials. Furthermore, THz radiation is believed to pose no more than minimal health risks to either a person being scanned or the operator of the system.

Presently available THz imaging techniques employ receivers that can be operated in a super-heterodyne configuration. The super-heterodyne approach is a relatively simple and low-cost approach that uses a single low noise amplifier (LNA) gain stage, a mixer, a local oscillator (LO) source and an intermediate frequency (IF) block. However, due to the relatively large number of receiver channels required, time synchronization of the local oscillation distribution may be critical. Direct-detection architectures may be employed to overcome the shortcomings of the super-heterodyne receivers. The direct-detection architecture entails use of a high gain LNA cascade, bandpass filtering, a high sensitivity detector and direct current (DC) electronics for noise voltage amplification. Unfortunately, these direct-detection receivers require a high level of gain in the low noise amplification stages with a flat gain response in order to amplify the scene noise floor above the noise floor of a detector diode. Furthermore, controlling this level of gain at the module level may be an onerous task as oscillation and unwanted feedback may occur especially as the operating frequency is increased.

There is therefore a need for a THz imaging system capable of real-time imaging. In particular, there is a significant need for a design of a THz imaging system for real-time imaging for use in security standoff detection applications. Also, it would be desirable to develop a simple and cost-effective method of fabricating a THz imaging system capable of real-time three-dimensional imaging.

BRIEF DESCRIPTION

Briefly, in accordance with aspects of the invention, a security detection system is presented. The system includes a radiation source configured to generate and direct terahertz radiation onto an object. Further, the system also includes a detector module configured to detect and process radiation from the object, the detector module comprising a parallel arrangement of at least two low noise amplifiers, each operable in a respective frequency band.

In accordance with further aspects of the invention, a security detection system is presented. The system includes a radiation source configured to generate and direct terahertz radiation onto an object. Furthermore, the system includes a receiver front end configured to receive radiation from the object. The system also includes a power splitter operatively coupled to the receiver front end and configured to split the detected radiation signal into at least two component signals, wherein each of the at least two component signals is attenuated to a different level. In addition, the system includes at least two processing channels in operative association with the power splitter, wherein each of the at least two processing channels is configured to process a respective one of the at least two component signals to generate a respective processed signal. Also, the system includes a digital signal processing module operatively coupled to the at least two processing channels and configured to combine the processed signals to generate a composite signal representative of the detected radiation.

In accordance with yet another aspect of the invention, a method for processing radiation is presented. The method includes irradiating an object with terahertz radiation. Additionally, the method includes detecting radiation from the object. The method also includes processing the detected radiation via a detector module having a distributed arrangement of low noise amplifiers.

In accordance with further aspects of the invention, a method for processing radiation is presented. The method includes irradiating an object with terahertz radiation. Additionally, the method includes detecting radiation from the object. The method also includes splitting the detected radiation into at least two component signals, wherein each of the at least two component signals is attenuated to a different level. Furthermore, the method includes processing each of the at least two component signals via a first limiter to generate a respective first limited signal, amplifying each of the first limited signals to generate a respective amplified signal. The method also includes processing each of the amplified signals via a second limiter to generate a respective second limited signal and processing each of the second limited signals via an analog-to-digital converter to generate a respective digital output signal representative of the respective processed signal. In addition, the method includes combining each of the processed signals to generate a composite signal representative of the detected radiation.

In accordance with further aspects of the invention, a security detection system is presented. The system includes a radiation source configured to generate and direct terahertz radiation onto an object. Furthermore, the system includes a detector module configured to detect and process radiation from the object, wherein the detector module comprises an parallel arrangement of at least two low noise amplifiers, wherein each low noise amplifier is configured to be operable in a respective frequency band. The system also includes a system controller configured to acquire one or more sets of detected radiation data from the detector module. Additionally, the system includes a computer system operationally coupled to the radiation source and the detector module, wherein the computer system is configured to facilitate receiving the one or more sets of detected radiation data.

DRAWINGS

These and other features, aspects, and advantages of the invention will become better understood when the following detailed description is read with reference to the accompanying drawings in which like characters represent like parts throughout the drawings, wherein.

DETAILED DESCRIPTION

Security detection systems for imaging in the THz frequency range are being increasingly employed in various applications. For example, security detection systems are utilized to detect materials of interest, such as, but not limited to, concealed weapons and/or explosives by scanning persons and/or objects in open areas such as airports and stations. Current THz imaging techniques employ receivers arranged in a super-heterodyne configuration. However, these super-heterodyne receivers suffer from drawbacks associated with time synchronization of local oscillation distribution. Direct-detection architectures have been used to mitigate the problems associated with the super-heterodyne receivers. Unfortunately, these direct-detection based systems require a high level of gain in the LNA stages. It may therefore be desirable to develop a robust technique that advantageously facilitates real-time imaging for use in security standoff detection applications. The techniques discussed herein address some or all of these issues.

Although, the exemplary embodiments illustrated hereinafter are described in the context of a security detection system for use in detecting concealed explosives and/or weapons on a person, it will be appreciated that use of the security detection system in a variety of security applications, such as, but not limited to, detection of explosives in parcels and luggage are also contemplated in conjunction with the invention.

Figure 1:
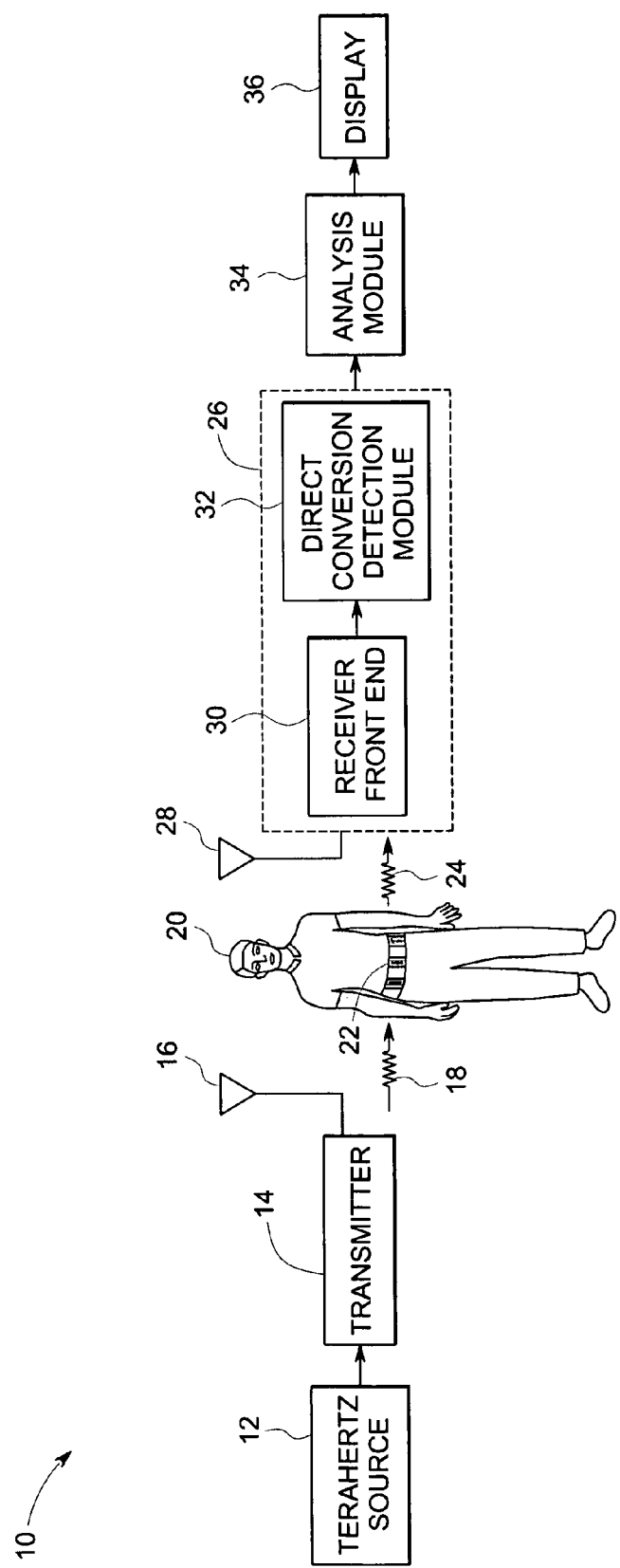
FIG. 1 is a block diagram of an exemplary security standoff detection system, in accordance with aspects of the invention.

FIG. 1 is a block diagram of an exemplary system 10 for use in security standoff detection in accordance with aspects of the invention. As will be appreciated, in a standoff detection system, a THz transmitter and a detector may be spaced at a distance of greater than three meters. Additionally, the standoff detection system may be gainfully employed for long-range screening and detection, and potentially offers a solution for scanning people in open areas such as airports and stations.

In the illustrated embodiment, the exemplary security standoff detection system 10 may be configured to facilitate detection of a material of interest on a person or in a parcel or luggage. As used herein, a "material of interest" may include concealed weapons, an explosive material, narcotics, biological agents or chemical agents. It may be noted that figures are drawn for illustrative purposes and are not drawn to scale. In the illustrated embodiment the exemplary security standoff detection system 10 is shown as including a radiation source 12. In one embodiment, the radiation source 12 may be a terahertz (THz) source, for example. In accordance with aspects of the invention, the THz source 12 may be configured to generate and direct THz radiation onto an object 20. Further, in certain embodiments, the radiation generated by the THz source 12 may be in a range from about 0.1 THz to about 10 THz. In a presently contemplated embodiment of the security standoff detection system 10, the radiation source 12 is shown as being in operative association with a transmitter 14. The source 12 may be configured to transmit THz radiation onto the object 20 via the transmitter 14. Also, the transmitter 14 is operatively coupled to a transmitting antenna 16. The security detection system 10 may be configured to transmit the THz radiation generated by the THz source 12 via the transmitting antenna 16.

Additionally, reference numeral 18 represents THz radiation that is incident on the object 20. Furthermore, in the illustrated embodiment, reference numeral 22 is indicative of an explosive material that may be concealed on the person 20. As previously noted, although the embodiments illustrated are described in the context of a security detection system used to detect hidden weapons and/or explosives 22 on a person 20, detection of weapons, explosives and/or chemical and biological agents in parcels and luggage are also contemplated in conjunction with the invention.

The security detection system 10 may include a receiving station 26. As used herein "receiving station" 26 refers to a module that includes a receiving antenna 28, a receiver front-end 30 and an exemplary direct conversion detection module 32. In accordance with aspects of the invention, the receiving station 26 may be configured to detect and process radiation 24 from the object 20. It may be noted that the radiation 24 may include radiation transmitted through the object 20, reflected from the object 20 or combinations thereof. The receiving antenna 28 may be configured to facilitate receiving the THz radiation 24. Moreover, the receiver front-end 30 may be configured to receive the radiation 24 from the receiving antenna 28.

Further, the exemplary direct conversion detection module 32 may include a parallel arrangement of at least two low noise amplifiers (LNAs), where each of the at least two LNAs are operable in a respective frequency band. This exemplary parallel arrangement of LNAs will be described in greater detail with reference to FIG. 2. In addition, the direct conversion detection module 32 may be configured to generate a processed signal representative of the detected radiation 24.

The processed signal generated by the direct conversion detection module 32 may then be analyzed by an analysis module 34. For example, the analysis module 34 may be configured to facilitate detection of an explosive material via analysis of the processed signal. The explosive material, if any, may then be displayed on a display module 36, for instance.

As previously noted, presently available THz imaging techniques employ receivers that may be operated in a super-heterodyne configuration. The super-heterodyne approach is a relatively simple and low-cost approach that uses a single LNA gain stage, a mixer, a local oscillator source and an intermediate frequency block. Due to the relatively large number of receiver channels required, time synchronization of the local oscillation distribution may be critical. The drawbacks associated with the super-heterodyne receivers may be circumvented by employing direct-detection architectures. The direct-detection architecture entails use of a high gain LNA cascade, bandpass filtering, a high sensitivity detector and direct current electronics for noise voltage amplification. Unfortunately, these direct-detection receivers require a high level of gain in the low noise amplification stages with a flat gain response in order to amplify the scene noise floor above the noise floor of a detector diode. Furthermore, controlling this level of gain at the module level may be a tedious task.

Figure 2:
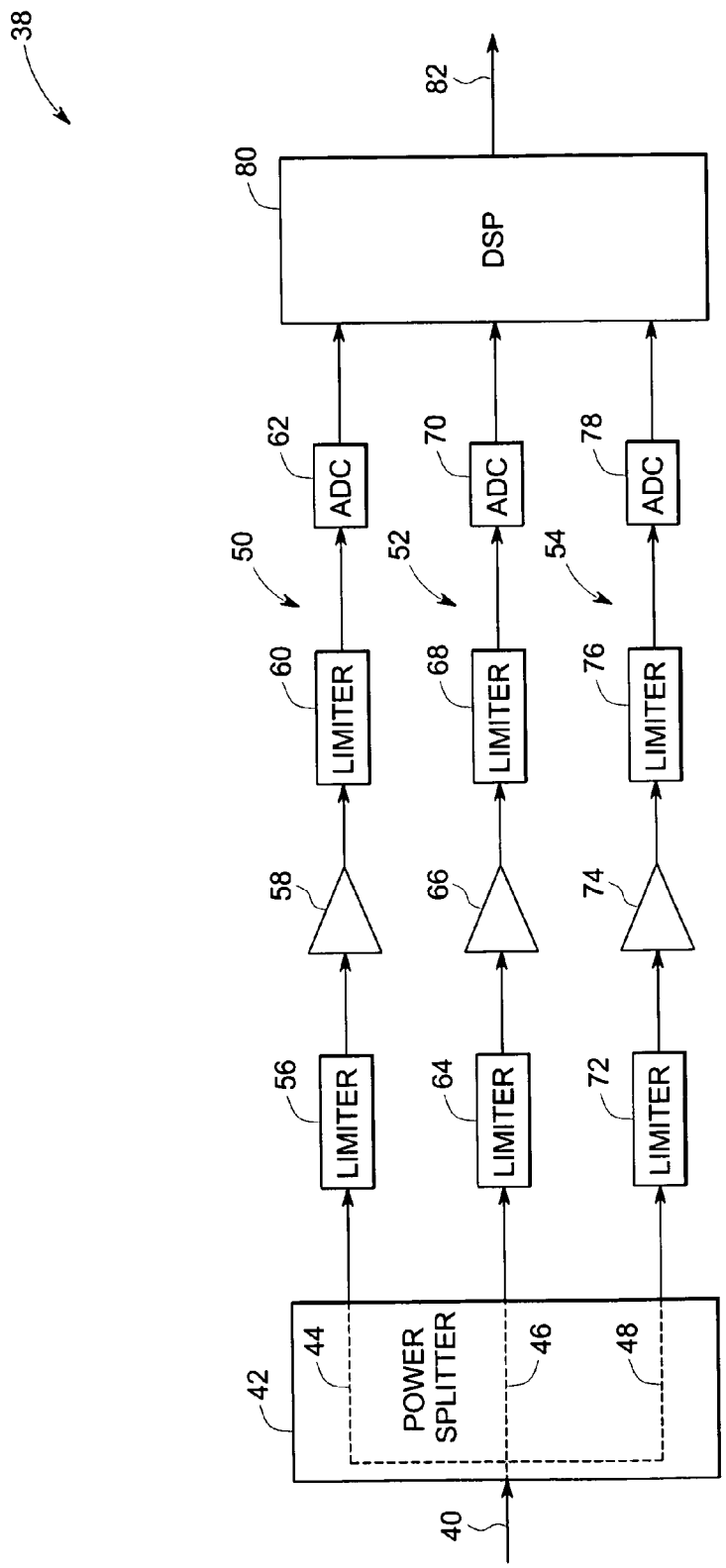
FIG. 2 is a block diagram of an exemplary detector module for use in the security standoff detection system illustrated in FIG. 1, in accordance with aspects of the invention.

In accordance with aspects of the invention, an exemplary direct conversion detection module that circumvents the drawbacks of the currently available direct-detection architectures is presented. FIG. 2 illustrates an exemplary embodiment of an architecture 38 of the direct conversion detection module 32 of FIG. 1 in greater detail. The exemplary direct conversion detection module 38 may be configured to facilitate processing detected radiation to detect and identify presence of a material of interest, where the direction conversion detection module 38 may include a parallel arrangement of at least two LNAs. It should be noted that each of the at least two LNAs is operable in a respective frequency band.

As will be appreciated, presently available ADCs are incapable of processing relatively high frequencies typically encountered in THz radiation. Additionally, current THz imaging techniques are known to employ a cascade of high gain LNAs. These shortcomings may be overcome by splitting the high frequency detected radiation signal into a plurality of component signals having relatively low frequencies. In other words, in accordance with aspects of the invention, these component signals may be simultaneously processed in a parallel fashion employing the currently available LNAs and ADCs.

In the illustrated embodiment, the direct conversion detection module 38 is illustrated as having a power splitter 42 that is configured to split detected radiation 40 into a plurality of component signals, wherein each of the plurality of component signals is attenuated to a different level. The detected radiation 40 is representative of radiation transmitted through the object, reflected from the object or combinations thereof. In the illustrated embodiment, the detected radiation 40 is shown as being split by the power splitter 42 into a first component signal 44, a second component signal 46 and a third component signal 48, where each of the component signals is attenuated to a different level. However, as will be appreciated, the power splitter 42 may also be configured to split the detected radiation signal 40 into more than three component signals.

Furthermore, in one embodiment, each of the three component signals 44, 46, 48 may be attenuated such that the an attenuation of the first component signal 44 is relatively less than an attenuation of the second component signal 46 and an attenuation of the third component signal 48. For example, the first component signal may be attenuated by about 20 decibels, the second component signal 46 may be attenuated by about 40 decibels, while the third component signal 48 may be attenuated by about 60 decibels.

Subsequently, each of the component signals 44, 46, 48 may be simultaneously processed via a respective processing channel. The processing channels may be configured to generate a respective processed component signal. In a presently contemplated configuration, the direct conversion detection module 38 is illustrated as having a first processing channel 50, a second processing channel 52 and a third processing channel 54, where each of the processing channels may be configured to process a respective component signal. For instance, the first processing channel 50 may be configured to process the first component signal 44. Similarly, the second processing channel 52 may be configured to process the second component signal 46, while the third processing channel 54 may be configured to process the third component signal 48. It may be noted that the direct conversion detection module 38 may include a desired number of processing channels such that the number of processing channels is related to the number of component signals generated by the power splitter 42.

As previously noted, each of the component signals generated by the power splitter 42 may be processed via a respective processing channel to generate a respective processed component signal. A limiter 56, a first low noise amplifier (LNA) 58, a limiter 60, and a first analog-to-digital converter (ADC) 62 may be serially coupled to form the first processing channel 50. The first component signal 44 may be processed via the limiter 56 to generate a first limited signal. In the illustrated embodiment, the first limiter 56 may be configured to facilitate a good impedance match between an output of the power splitter 42 and an input of the LNA 58 for a broad frequency spectrum.

Subsequently, this first limited signal may be amplified via the first LNA 58. As will be appreciated, the first LNA 58 is typically a preamplifier that is configured to amplify very weak first component signal 44. Consequent to amplification by the first LNA 58, an amplified signal may be generated.

Following amplification, the amplified signal may be further processed via the second limiter 60 to generate a second limited signal. The second limiter 60 may be configured to facilitate a good impedance match between an output of the LNA 58 and an input of the ADC 62. An output of the limiter 60, the second limited signal, may be processed via the ADC 62 to obtain a digital output signal. This digital output signal may be referred to as a first processed component signal, where the first processed component signal is representative of the first component signal 44. The ADC 62 may be configured to aid in broadband conversion and to deliver the attenuated component signal for signal reconstruction based on signal processing methods.

In a similar fashion, a limiter 64, a second LNA 66, a limiter 68, and a second ADC 70 may be serially coupled to form the second processing channel 52. As with the first processing channel 50, the second component signal 46 may be processed along the second processing channel 52 via the limiter 64 and amplified by the second LNA 66. An output of the second LNA 66, a second amplified signal, may be further processed via the limiter 68, as previously described. Furthermore, an output of the limiter 68 may be converted to a second digital output signal by the second ADC 70. Subsequent to this processing, a second processed component signal representative of the second component signal 46 is generated by the second processing channel 52.

As described with reference to the first and second processing channels 50, 52, a limiter 72, a third LNA 74, a limiter 76, and a third ADC 78 may be serially coupled to form the third processing channel 54. The third component signal 48 may be processed along the third processing channel 54 via the limiter 72 and amplified by the third LNA 74. As previously described, the amplified signal may be further processed via the limiter 76 and converted to a digital output signal via the third ADC 78. Subsequent to the processing, a third processed component signal, representative of the third component signal 48, is generated by the third processing channel 54.

As previously noted, the direct conversion detection module 38 includes a parallel arrangement of a plurality of LNAs, where each of the plurality of LNAs is operable in a respective frequency band. In a presently contemplated configuration, three LNAs 58, 66, 74 are arranged in a parallel arrangement to facilitate parallel processing of the plurality of component signals 44, 46, 48. It may be noted that, in one embodiment, each of the three LNAs 58, 66, 74 may be configured such that each of the LNAs has a different gain to deliver a desired dynamic range and noise performance. For instance, a gain of the first LNA 58 may be configured to be relatively greater than a gain of the second LNA 66 and a gain of the third LNA 74. For example, the gain of the first LNA 58 may be 20 decibels (dB), the gain of the second LNA may be 30 dB, while the gain of the third LNA 74 may be 40 dB.

By implementing the LNAs in an exemplary parallel arrangement as described hereinabove, use of a high gain LNA cascade typically employed in current THz imaging techniques may be circumvented. In addition, presently available ADCs may be utilized to process the individual component signals having relatively low frequencies.

Consequent to the processing of the three component signals 44, 46, 48 via respective processing channels 50, 52, 54, respective digital signals representative of corresponding component signals are generated. In a presently contemplated configuration, the direct conversion detection module 38 may include a digital signal processing (DSP) module 80. The DSP module 80 may be configured to receive the plurality of processed component signals generated by respective processing channels and combine the processed component signals to generate a single, digital composite signal 82. In other words, the DSP module 80 may be configured to combine the plurality of component signals that have been attenuated to different levels and amplified to different levels to reconstruct the detected radiation signal 40. Accordingly, the composite signal 82 generated by the DSP module 80 is representative of the detected radiation 40.

This composite signal 82 may then be processed via an analysis module, such as the analysis module 34 (see FIG. 1). In one embodiment, the analysis module may be configured to process the composite signal 82 to facilitate detection of presence of a variety of materials of interest for security applications, such as, but not limited to, concealed explosives, weapons, chemical and biological agents. Each of these materials of interest is known to exhibit characteristic THz spectra that may be employed to fingerprint and thereby identify these materials of interest. Accordingly, predetermined features, such as THz spectra, may be employed to aid in the detection and identification of materials of interest. Subsequent to the analysis of the composite signal 82 by the analysis module, the detected materials of interest, if any, may be displayed on a display module, such as the display module 36 (see FIG. 1) to facilitate a user to easily visualize any detected materials of interest, such as concealed weapons and/or explosive material, for example.

Figure 3:
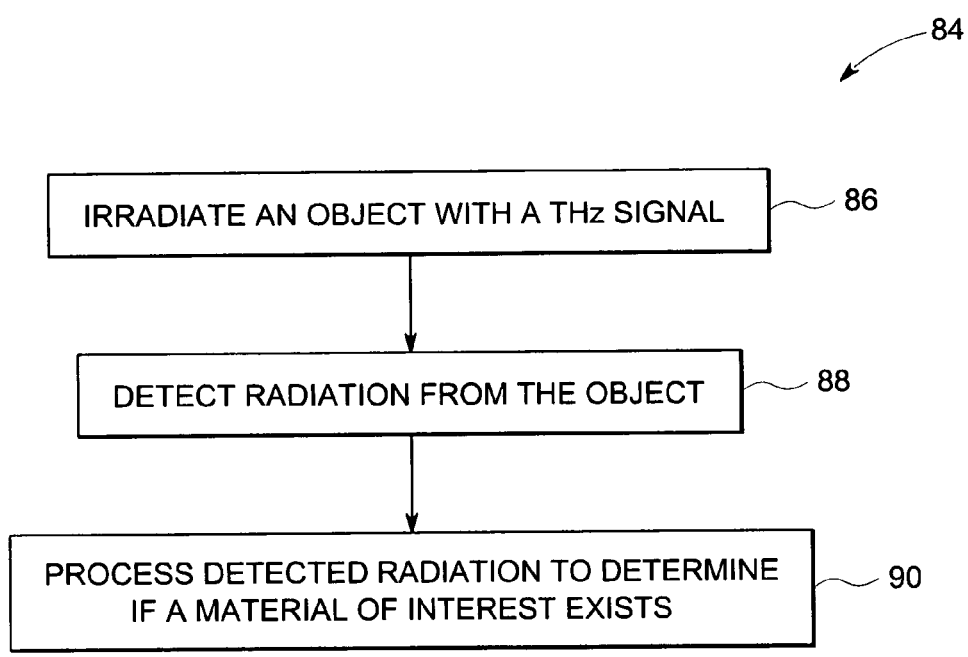
FIG. 3 is a flow chart depicting an exemplary process for security standoff detection, in accordance with aspects of the invention.

Turning now to FIG. 3, a flow chart of exemplary logic 84 for processing detected THz radiation is illustrated. In accordance with exemplary aspects of the invention, a method for processing detected radiation for use in a security standoff detection system is presented. The method starts at step 86 where an object may be irradiated with a THz signal. As previously noted, a THz source capable of generating and directing THz radiation towards the object may be utilized to irradiate the object. In one embodiment, the object may include a person, while in other embodiments, the object may include a parcel or luggage.

At step 88, THz radiation from the object may be detected via an exemplary direct conversion detection module, in accordance with aspects of the invention. In certain embodiments, THz radiation transmitted through the object may be detected. Alternatively, in certain other embodiments, THz radiation reflected from the object may be detected. However, it may be noted that a combination of THz radiation transmitted through the object and THz radiation reflected from the object may also be detected. Following step 88, the detected radiation signal may be processed at step 90 to determine if a material of interest exists. The method of processing the detected radiation to determine if a material of interest exists will be defined in greater detail with reference to FIGS. 4-5.

Figure 4:
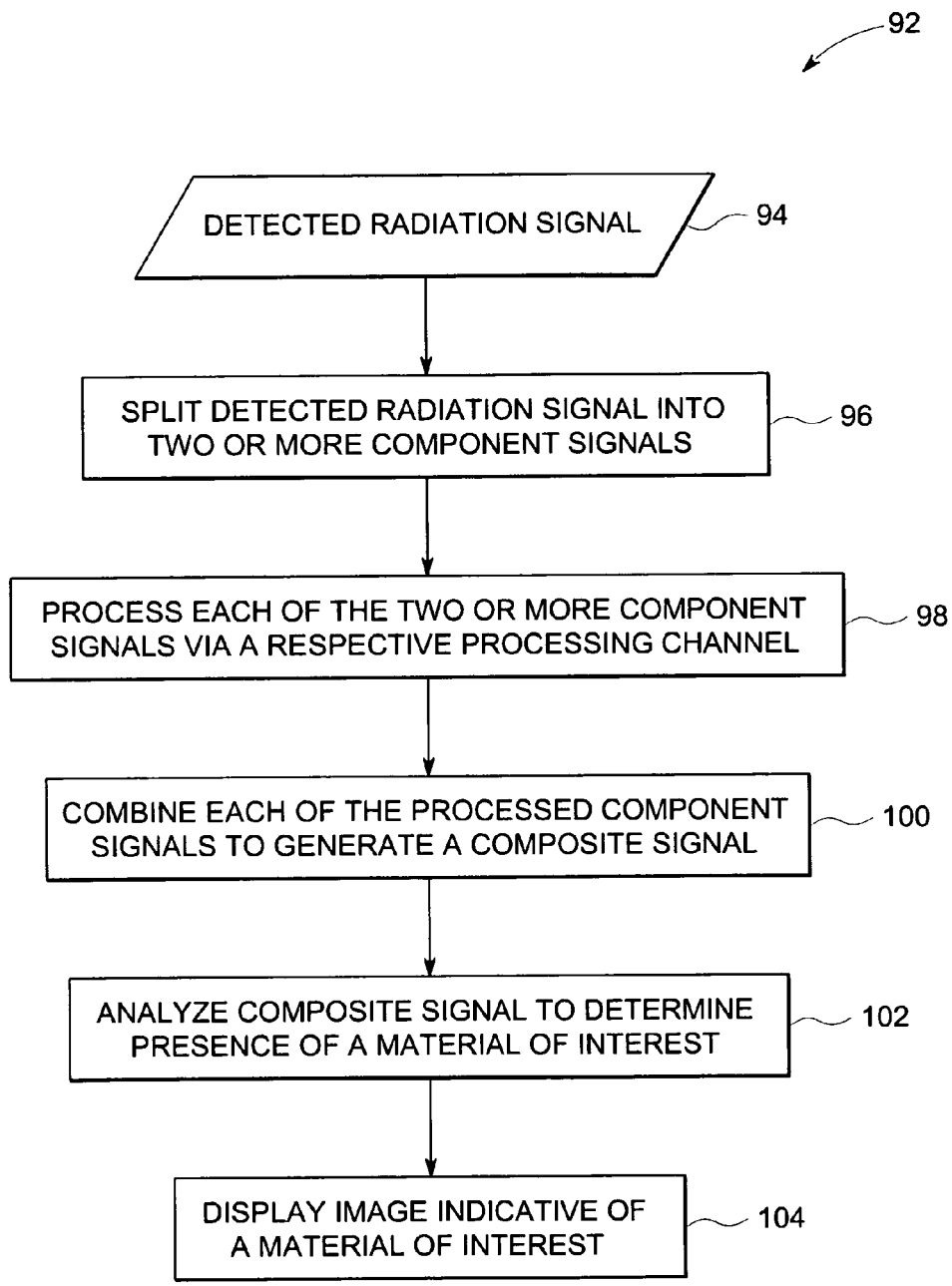
FIG. 4 is a flow chart depicting an exemplary process for detecting radiation and processing detected radiation, in accordance with aspects of the invention.

Referring now to FIG. 4, a flow chart illustrating exemplary logic 92 for a method of processing a detected radiation signal 94 via an exemplary direct conversion detection module is depicted. As previously described, in accordance with exemplary aspects of the invention, the direct conversion detection module (see FIG. 2) may include a power splitter that is configured to split the detected radiation signal in two or more component signals. Accordingly, at step 96, the detected radiation signal is split into a plurality of component signals. Further, each of the component signals is attenuated to a different level, as previously described with reference to FIG. 2. Subsequently, at step 98, each of these component signals may be processed via a respective processing channel to generate a respective processed component signal. The method of processing each of the component signals will be described in greater detail with reference to FIG. 5.

Following step 98, each of the processed component signals may be combined at step 100 to generate a composite signal, where the composite signal is representative of the detected radiation signal. In one embodiment, a DSP module may be employed to facilitate combining the plurality of processed component signals, where each of the plurality of processed component signals has been attenuated to a different level. The combined composite signal may then be analyzed at step 102 to determine if any material of interest, such as an explosive material, exists. An image may then be generated and displayed at step 104. The displayed image may aid a user in visualizing presence of any explosive material.

Figure 5:
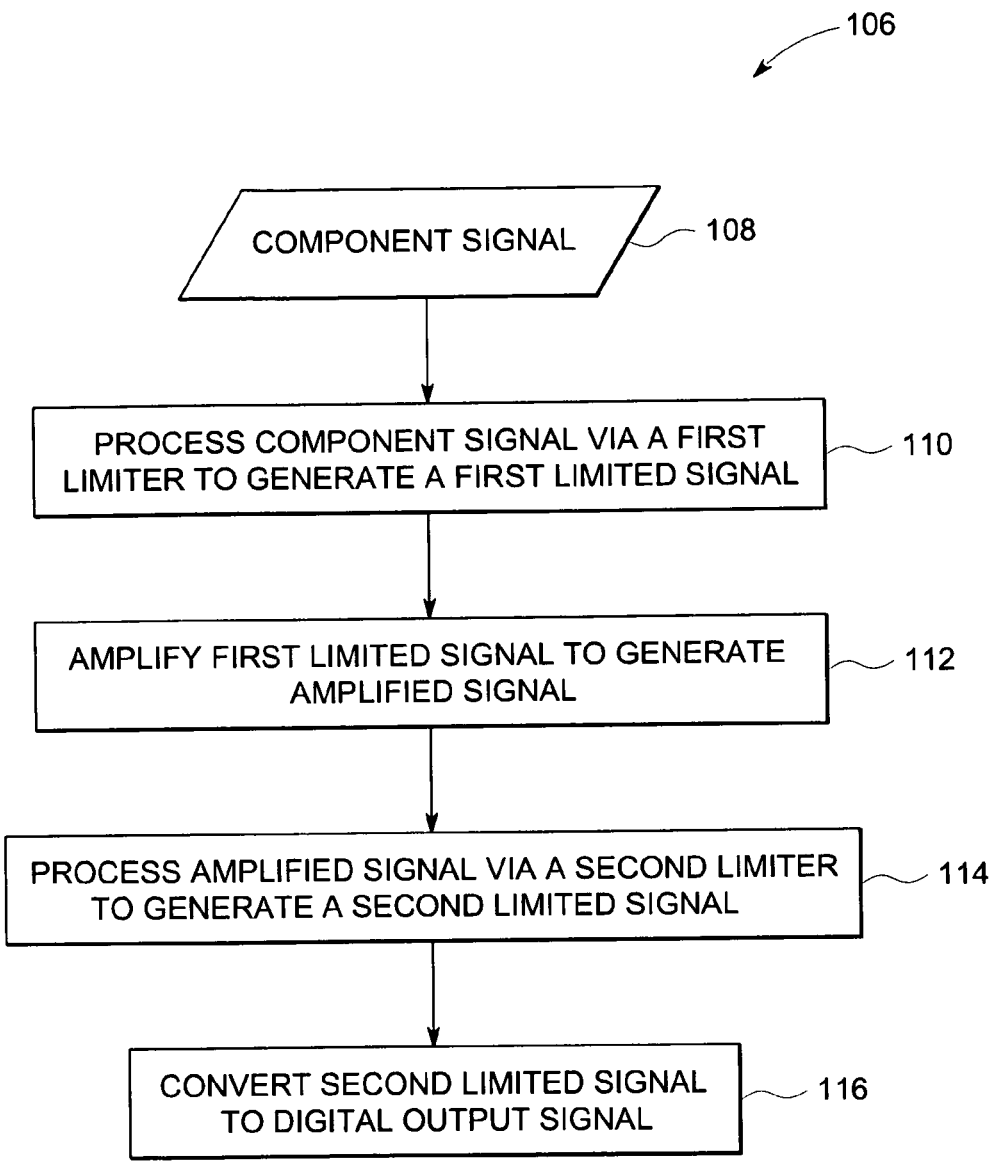
FIG. 5 is a flow chart depicting an exemplary process for processing detected radiation, in accordance with aspects of the invention.

FIG. 5 illustrates exemplary logic 106 for processing each of the component signals 108 via a respective processing channel. The method starts at step 110 where the component signal 108 is processed via a first limiter. The first limiter may be configured to process the component signal 108 and generate a first limited signal. At step 112, this first limited signal may be amplified via a LNA to generate an amplified signal. As will be appreciated, a LNA may be employed to amplify very weak detected radiation signal captured by the receiving antenna 28 (see FIG. 1). Consequent to amplification by the LNA, an amplified signal may be generated. The amplified signal may then be processed via a second limiter at step 114. A second limited signal may be generated consequent to processing the amplified signal via the second limiter. Additionally, at step 116, the second limited signal may be processed via an ADC to generate a digital output signal. This digital output signal is representative of a processed component signal.

In accordance with exemplary aspects of the invention, each of the plurality of component signals may be simultaneously processed via a respective parallel processing channel. In other words, each of the component signals may be simultaneously processed via steps 110-116.

The security standoff detection system 10 illustrated in FIG. 1 may find application in a variety of security applications. For example, the security detection system 10 may find application in detection of concealed weapons and/or explosives on a person, in luggage or in parcels. As will be appreciated, the use of the security detection system described hereinabove has given rise to numerous new possibilities enabling enhanced speed of operation and overall cost reduction.

Also, as the high frequency detected radiation signal is split into a plurality of component signals having relatively low frequencies, each of the plurality of component signals may be simultaneously processed via a single respective LNA. By implementing the direct conversion detection module 38 having a plurality of LNAs in a parallel arrangement, use of high gain LNA cascades employed by current techniques may be circumvented. Furthermore, this exemplary parallel arrangement of LNAs advantageously enhances stability of the direct conversion detection module 38 as the present arrangement does not call for control of LNA gain.

Additionally, current ADCs are not configured to process signals having relatively high frequencies typically encountered in THz radiation. By implementing the direct conversion detection module 38 such that the detected radiation signal 40 is split into a plurality of component signals having relatively low frequencies, currently available ADCs may be employed to process the component signals having relatively low frequencies. Also, disadvantages associated with use of local oscillators (LOs) may be mitigated thereby advantageously reducing cost associated with the security system 10 (see FIG. 1). Furthermore, the methods of processing detected radiation described hereinabove advantageously facilitate real-time imaging of persons, packages and luggage to aid in the detection of concealed weapons, explosives, biological and chemical agents.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A security detection system, comprising:
   a radiation source for generating and directing terahertz radiation onto an object; and
   a detector module for detecting and processing radiation from the object, the detector module comprising a power splitter for splitting the detected radiation into at least two component signals, each of the at least two component signals being attenuated to a different level.

2. The security detection system of claim 1, wherein the detector module comprises a receiver front end configured to receive the radiation from the object.

3. The security detection system of claim 1, wherein the detector module comprises a parallel arrangement of at least two low noise amplifiers, each operable in a respective frequency band and configured to process a respective one of the at least two component signals.

4. The security detection system of claim 1, wherein the detector module comprises at least two processing channels configured to process a respective one of the at least two component signals to generate a respective processed signal.

5. The security detection system of claim 4, wherein the at least two processing channels each comprises:
   a first limiter configured to process a respective component signal to generate a respective first limited signal;
   a low noise amplifier configured to amplify the respective first limited signal to generate a respective amplified signal;
   a second limiter configured to process the respective amplified signal to generate a respective second limited signal; and
   an analog-to-digital converter configured to process the respective second limited signal to generate a respective digital output signal representative of the respective processed signal.

6. The security detection system of claim 4, wherein the detector module comprises a digital signal processing module for combining the at least two processed signals to generate a composite signal representative of the detected radiation.

7. The security detection system of claim 6, comprising an analysis module for analyzing the composite signal to determine if one or more predetermined features of an explosive material exist.

8. The security detection system of claim 7, comprising a display module for facilitating display of the one or more predetermined features.

9. A security detection system, comprising:
   a radiation source configured to generate and direct terahertz radiation onto an object;
   a receiver front end configured to receive radiation from the object;
   a power splitter operatively coupled to the receiver front end and configured to split the detected radiation signal into at least two component signals, wherein each of the at least two component signals is attenuated to a different level;
   at least two processing channels in operative association with the power splitter, wherein each of the at least two processing channels is configured to process a respective one of the at least two component signals to generate a respective processed signal; and
   a digital signal processing module operatively coupled to the at least two processing channels and configured to combine the processed signals to generate a composite signal representative of the detected radiation.

10. The security detection system of claim 9, wherein the at least two processing channels each comprises:
   a first limiter operatively coupled to the power splitter and configured to process a respective component signal to generate a respective first limited signal;
   a low noise amplifier in operative association with the first limiter and configured to amplify a respective first limited signal to generate a respective amplified signal;
   a second limiter operatively coupled to the low noise amplifier and configured to process the respective amplified signal to generate a respective second limited signal; and
   an analog-to-digital converter in operative association with the second limiter and configured to process the respective second limited signal to generate a respective digital output signal representative of the respective processed signal.

11. The security detection system of claim 9, comprising an analysis module in operative association with the digital signal processing module, wherein the analysis module is configured to analyze the composite signal to determine if one or more predetermined features of an explosive material exist.

12. The security detection system of claim 11, comprising a display module operatively coupled to the analysis module, wherein the display module is configured to facilitate displaying the identified one or more predetermined features.

13. A method for processing radiation, the method comprising:
 irradiating an object with terahertz radiation;
 detecting radiation from the object; and
 processing the detected radiation via a detector module having a distributed arrangement of low noise amplifiers, wherein processing comprises splitting the detected radiation into at least two component signals attenuated to different levels.

14. The method of claim 13, wherein said irradiating the object comprises generating and directing terahertz radiation onto the object.

15. The method of claim 13, wherein said processing the detected radiation comprises:
 processing the at least two component signals via a respective processing channel to generate a respective processed signal; and
 combining each of the processed signals to generate a composite signal representative of the detected radiation.

16. The method of claim 15, wherein said processing the at least two component signals comprises:
 processing each of the at least two component signals via a first limiter to generate a respective first limited signal;
 amplifying each of the first limited signals to generate a respective amplified signal;
 processing each of the amplified signals via a second limiter to generate a respective second limited signal; and
 processing each of the second limited signals via an analog-to-digital converter to generate a respective digital output signal representative of the respective processed signal.

17. The method of claim 15, further comprising analyzing the composite signal to determine if one or more predetermined features of an explosive material exist.

18. The method of claim 17, further comprising displaying the identified one or more predetermined features.

19. A method for processing radiation, the method comprising:
 irradiating an object terahertz radiation;
 detecting radiation from the object;
 splitting the detected radiation into at least two component signals, wherein each of the at least two component signals is attenuated to a different level;
 processing each of the at least two component signals via a first limiter to generate a respective first limited signal;
 amplifying each of the first limited signals to generate a respective amplified signal;
 processing each of the amplified signals via a second limiter to generate a respective second limited signal;
 processing each of the second limited signals via an analog-to-digital converter to generate a respective digital output signal representative of the respective processed signal; and
 combining each of the processed signals to generate a composite signal representative of the detected radiation.

20. The method of claim 19, wherein said irradiating the object comprises generating and directing terahertz radiation onto the object.

21. The method of claim 19, further comprising analyzing the composite signal to determine if one or more predetermined features of an explosive material exist.

22. The method of claim 21, further comprising displaying the identified one or more predetermined features.

23. A security detection system, comprising:
 a radiation source configured to generate and direct terahertz radiation onto an object;
 a detector module configured to detect and process radiation from the object, wherein the detector module comprises a receiver front end configured to receive radiation from the object and a power splitter in operative association with the receiver front end and configured to split the detected radiation signal into at least two component signals;
 a system controller configured to acquire one or more sets of detected radiation data from the detector module; and
 a computer system operationally coupled to the radiation source and the detector module, wherein the computer system is configured to facilitate receiving the one or more sets of detected radiation data.

24. The security detection system of claim 23, wherein the detector module comprises:
 at least two processing channels operatively coupled to the power splitter and configured to process a respective component signal to generate a respective processed signal, the at least two processing channel comprising a parallel arrangement of at least two low noise amplifiers operable in respective frequency bands; and
 a digital signal processing module operatively coupled to the at least two processing channels and configured to combine the processed signals to generate a composite signal representative of the detected radiation.

25. The security detection system of claim 24, further comprising an analysis module configured to analyze the composite signal to determine if one or more predetermined features of an explosive material exist.

26. The security detection system of claim 25, further comprising a display module configured to facilitate displaying the identified one or more predetermined features.

* * * * *